US010851192B2

(12) United States Patent
Loy et al.

(10) Patent No.: US 10,851,192 B2
(45) Date of Patent: Dec. 1, 2020

(54) DIHYDROPYRIDAZINE-BASED ANTIOXIDANTS AND USES THEREOF

(71) Applicant: ARIZONA BOARD OF REGENTS ON BEHALF OF THE UNIVERSITY OF ARIZONA, Tucson, AZ (US)

(72) Inventors: Douglas A. Loy, Tucson, AZ (US); Robb E. Bagge, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/969,608

(22) Filed: May 2, 2018

(65) Prior Publication Data

US 2018/0244820 A1 Aug. 30, 2018

Related U.S. Application Data

(63) Continuation-in-part of application No. 15/751,797, filed as application No. PCT/US2016/046199 on Aug. 9, 2016, now Pat. No. 10,619,023.

(60) Provisional application No. 62/500,378, filed on May 2, 2017, provisional application No. 62/269,564, filed on Dec. 18, 2015, provisional application No. 62/203,828, filed on Aug. 11, 2015.

(51) Int. Cl.
*C08F 236/20* (2006.01)
*C07D 237/04* (2006.01)

(52) U.S. Cl.
CPC .......... *C08F 236/20* (2013.01); *C07D 237/04* (2013.01)

(58) Field of Classification Search
CPC ................................ C07D 237/04; C08F 8/48
See application file for complete search history.

(56) References Cited

U.S. PATENT DOCUMENTS

| | | | |
|---|---|---|---|
| 3,022,305 A * | 2/1962 | Carboni | C07D 487/08 544/224 |
| 4,559,369 A | 12/1985 | Bauman | |
| 4,704,408 A | 11/1987 | Krug | |
| 5,034,463 A | 7/1991 | Brokken-Zijp et al. | |
| 6,534,611 B1 | 3/2003 | Darling et al. | |
| 6,866,045 B1 | 3/2005 | Maillard et al. | |
| 2004/0262217 A1 | 12/2004 | Mori et al. | |
| 2004/0266940 A1 | 12/2004 | Issari | |
| 2009/0253015 A1 | 10/2009 | Onodera et al. | |
| 2009/0264544 A1 | 10/2009 | Loy | |
| 2010/0016545 A1 | 1/2010 | Wiessler et al. | |
| 2011/0171076 A1 | 7/2011 | Fansler et al. | |
| 2013/0253120 A1 | 9/2013 | Kulkarni et al. | |
| 2013/0261272 A1 | 10/2013 | Herzog et al. | |
| 2014/0113844 A1* | 4/2014 | Haque | C10M 143/04 508/131 |
| 2014/0371396 A1 | 12/2014 | Van Rheenen et al. | |

FOREIGN PATENT DOCUMENTS

| | | |
|---|---|---|
| WO | WO2004047568 A1 | 6/2004 |
| WO | WO2009134227 A1 | 11/2009 |
| WO | WO2015121336 A1 | 8/2015 |
| WO | WO2015154078 A1 | 10/2015 |

OTHER PUBLICATIONS

Knall, Chem. Commun., 2013, 49, p. 7325-7327 (Year: 2013).*
Kang, JW et al. Low-Loss Fluorinated Poly(Arylene Ether Sulfide) Waveguides with High 12.33Thermal Stability. Journal of Lightwave Technology. vol. 19. No. 6. Jun. 2001, pp. 872-875.
Loy D.A., Tetrazines for hydrogen storage. 59-th Annual Report on Research 2014 [online]. 55-57 Report 50941-ND7. 2014 (2014) [retrieved on Aug. 30, 2017). retrieved from the Internet: <https:Ilacswebcontent.acs.org/prfar/2014/Paper13084.html>. pp. 1-5.
Al-Malaika, S. In Reactive antioxidants for polymers, 1997; Blackie: 1997; pp. 266-302.
Heim, K. C. Natural polyphenol and flavonoid polymers. In: Cirillo G, Iemma F, eds. Antioxidant Polymers: Synthesis, Properties and Applications. Hoboken, NJ: Scrivener Publishing LLC and John Wiley & Sons Ltd; 2012, pp. 23-54.
Lei, H.; Huang, G.; Weng, G., Synthesis of a New Nanosilica-Based Antioxidant and Its Influence on the Anti-Oxidation Performance of Natural Rubber. J. Macromol. Sci., Part B: Phys. 2013, 52, (1), 84-94.
Solera, P., New trends in polymer stabilization. J. Vinyl Addit. Technol. 1998, 4, (3), 197-210.
Cerna, A.; Cibulkova, Z.; Simon, P.; Uhlar, J.; Lehocky, P., DSC study of selected antioxidants and their binary mixtures in styrene-butadiene rubber. Polym. Degrad. Stab. 2012, 97, (9), 1724-1729.
Jaiswal, S.; Varma, P. C. R.; O'Neill, L.; Duffy, B.; McHale, P., An investigation of the biochemical properties of tetrazines as potential coating additives. Mat Sci Eng C-Mater 2013, 33, (4), 1925-1934.
Polezhaev, A. V.; Maciulis, N. A.; Chen, C.-H.; Pink, M.; Lord, R. L.; Caulton, K. G., Tetrazine Assists Reduction of Water by Phosphines: Application in the Mitsunobu Reaction. Chem.—Eur. J. 2016, 22, (39), 13985-13998.
Audebert, P.; Sadki, S.; Miomandre, F.; Clavier, G., First example of an electroactive polymer issued from an oligothiophene substituted tetrazine. Electrochem Commun 2004, 6, (2), 144-147.

(Continued)

*Primary Examiner* — Robert C Boyle
(74) *Attorney, Agent, or Firm* — Nguyen Tarbet LLC

(57) ABSTRACT

Dihydropyridazines compounds having antioxidant properties and uses thereof are described herein. These compounds can function as antioxidants that prevent oxidation of materials, including polymers, and as free radical inhibitors to stabilize reactive chemicals, such as monomers against free radical reactions. The dihydropyridazines can be added as small molecule additives or they can be incorporated into molecules bearing dienophilic C=C double bonds through a Carboni Lindsey reaction, which can reduce environmental and health exposure to antioxidants in plastics and allow for a greater quantity of the antioxidants to be used.

6 Claims, No Drawings

(56) References Cited

OTHER PUBLICATIONS

Fukuzumi, S.; Yuasa, J.; Suenobu, T., Scandium Ion-Promoted Reduction of Heterocyclic N:N Double Bond. Hydride Transfer vs Electron Transfer. J. Am. Chem. Soc. 2002, 124, (42), 12566-12573.

International Search Report Issued for PCT Application No. PCT/US16/46199 dated Jan. 26, 2017.

International Search Report Issued for PCT Application No. PCT/US17/24702 dated Jun. 27, 2017.

International Search Report Issued for PCT Application No. PCT/US17/25110 dated Jun. 22, 2017.

International Search Report Issued for PCT Application No. PCT/US17/40098 dated Sep. 29, 2017.

Alge et al. Synthetically Tractable Click Hydrogels for Three-Dimensional Cell Culture Formed Using Tetrazine-Norbornene Chemistry. Biomacromolecules. 2013, 14, 949-953.

Desai et al. Versatile click alginate hydrogels crosslinked via tetrazineenorbornene chemistry. Biomaterials 50 (2015) 30-37.

Sukwon Jung and Hyunmin Yi. An Integrated Approach for Enhanced Protein Conjugation and Capture with Viral Nanotemplates and Hydrogel Microparticle Platforms via Rapid Bioorthogonal Reactions. Langmuir. 2014, 30, 7762-7770.

Kawamoto et al. Dual Role for 1,2,4,5-Tetrazines in Polymer Networks: Combining Diels-Alder Reactions and Metal Coordination to Generate Functional Supramolecular Gels. ACS Macro Lett. 2015, 4, 458-461.

Knall et al. Inverse electron demand Diels-Alder (iEDDA) functionalisation of macroporous poly(dicyclopentadiene) foams. Chem. Commun., 2013, 49, 7325.

Liu et al. Theoretical Elucidation of the Origins of Substituent and Strain Effects on the Rates of Diels-Alder Reactions of 1,2,4,5-Tetrazines. J. Am. Chem. Soc. 2014, 136, 11483-11493.

Liu et al. Modular and orthogonal synthesis of hybrid polymers and networks. Chem. Commun., 2015, 51, 5218.

Tork et al. Molecular Dynamics of the Diels-Alder Reactions of Tetrazines with Alkenes and N2 Extrusions from Adducts. J. Am. Chem. Soc. 2015, 137, 4749-4758.

Zhang et al. Interfacial Bioorthogonal Cross-Linking. ACS Macro Lett. 2014, 3, 727-731.

Vazquez et al. Mechanism-Based Fluorogenic trans-Cyclooctene-Tetrazine Cycloaddition. Angew. Chem. Int. Ed. 2017, 56, 1334-1337.

Heldmann et al. Synthesis of Metallated (Metal = Si, Ge, Sn) Pyridazines by Cycloaddition of Metal Substituted Alkynes to 1,2,4,5-Tetrazine. Tetrahedron Letters, vol. 38, No. 33, pp. 5791-5794, 1997.

Sauer et al. 1,2,4,5-Tetrazine: Synthesis and Reactivity in [4l2] Cycloadditions. Eur. J. Org. Chem. 1998, 2885-2896.

* cited by examiner

DIHYDROPYRIDAZINE-BASED ANTIOXIDANTS AND USES THEREOF

CROSS REFERENCE

This application is a non-provisional and claims benefit of U.S. Provisional Application No. 62/500,378 filed May 2, 2017, the specification(s) of which is/are incorporated herein in their entirety by reference.

This application is a continuation-in-part and claims benefit of U.S. patent application Ser. No. 15/751,797 filed Feb. 9, 2018, which is a 371 and claims benefit of PCT/US16/46199 filed Aug. 9, 2016, which claims benefit of U.S. Provisional Application No. 62/269,564 filed Dec. 18, 2015 and U.S. Provisional Application No. 62/203,828 filed Aug. 11, 2015, the specification(s) of which is/are incorporated herein in their entirety by reference.

FIELD OF THE INVENTION

The present invention relates to compounds that may be used as antioxidants and free radical inhibitors, namely, compounds that are based on dihydropyridazines.

BACKGROUND OF THE INVENTION

Numerous chemical compounds that are used in industrial applications are prone to oxidative degradation. For example, certain conditions may induce the formation of free radicals in polymers, lubricants, coatings, and the like, which can be detrimental to product quality. Hence, manufacturers typically add antioxidizing agents and free radical inhibitors to preserve their products. Polymer degradation due to oxidation is the primary mechanism for the failure of elastomers, thermoplastics, and thermosets. Their failure can be delayed by the addition of antioxidants. However, current preservatives possess undesirable properties that can lead to other problems. For instance, butylated hydroxyanisole (BHA) and butylated hydroxytoluene (BHT) are common preservatives that are being scrutinized as endocrine disruptors and carcinogens. As another example, the addition of polymerization inhibitors can prolong the shelf-life of the polymer precursors; but may require an additional process to remove the inhibitors in order to maintain polymer purity. The preservatives can also become exhausted and over time, lose their effectiveness and stability. Hence, novel antioxidant compounds are needed as an alternative to existing technologies.

The present invention utilizes dihydropyridazines as antioxidants or free radical reaction inhibitors. Although there exist many antioxidants based on aromatic molecules modified with hydroxyl groups (phenols), amines (aryl amines), or phosphites, there have been no reports on dihydropyridazines being used as antioxidants. For example, Wang et al. teaches the use of 1,4-dihydropyridine as an antioxidant (Wang, L. F.; Zhang, H. Y.; Kong, L.; Chen, Z. W.; Shi, J. G., DFT calculations indicate that 1,4-dihydropyridine is a promising lead antioxidant. *Helv Chim Acta* 2004, 87, (6), 1515-1521). However, the 1,4-dihydropyridine compound contains only one nitrogen in the ring and said nitrogen is more difficult to recycle.

SUMMARY OF THE INVENTION

It is an objective of the present invention to provide for antioxidants and methods for inhibiting or retarding oxidative degradation, as specified in the independent claims. Embodiments of the invention are given in the dependent claims. Embodiments of the present invention can be freely combined with each other if they are not mutually exclusive.

The present invention utilizes dihydropyridazines as antioxidants for use in thermoplastics, thermosets and elastomers; free radical inhibitors to stabilize reactive chemicals, such as monomers against free radical polymerizations; and as anticorrosion agents in coatings to protect against metal oxidation. In some aspects, the present invention provides methods for inhibiting or delaying the oxidation of various oxidizable materials including, but not limited to, small molecules, polymers, metals, foods, and other materials prone to oxidation. These methods may comprise the addition of dihydropyridazines to various base substrates or oxidizable materials. In other aspects, the present invention provides methods for the preparing compositions having antioxidant properties. The resulting compositions may be used for pharmaceutical, cosmetic, packaging, coating, or other applications.

In some embodiments, a method for inhibiting or delaying oxidation of an oxidizable material may comprise adding an antioxidant to the oxidizable material. The antioxidant may comprise a dihydropyridazine compound present in an amount that is sufficient to inhibit or delay oxidation of said oxidizable material when the dihydropyridazine compound and oxidizable material are exposed to an oxidizing species, such as oxygen, a chemical oxidant, or a free radical generated by thermal processes, degradation of peroxides, ultraviolet light or ionizing radiation, or free radical initiators. The dihydropyridazine compound may be oxidized to consume the oxidizing species, thereby preventing or hindering the oxidizing species from oxidizing the oxidizable material.

In some embodiments, the dihydropyridazine compound may be prepared using by a reaction of tetrazine precursors with a polymer backbone having unreacted alkene functional groups, wherein the tetrazine precursors react with the alkene functional groups in the polymer backbone via a Carboni-Lindsey reaction, thereby covalently attaching a dihydropyridazine group to the polymer backbone; or condensation of 1,4-diones with hydrazine; or reduction of pyridazines.

In other embodiments, the dihydropyridazine compound may be a 1,4-dihydropyridazine according to the formula:

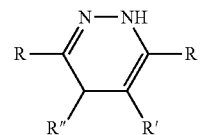

In one embodiment, R can be an H, Cl, Br, F, alkyl, aryl, pyridyl, O-alkyl, S-alkyl, S-aryl, $NH_2$, NH-Alkyl, NH-Aryl, N-(Alkyl)$_2$, N-(Aryl)$_2$, $NHNH_2$, N=CRR', vinyl, alkenyl, $CO_2$-Alkyl, $CO_2$-Aryl, $CONH_2$, CONH-Alkyl, CONH-Aryl, CON-(Alkyl)$_2$, CON-(Aryl)$_2$, or CN. In another embodiment, R' and R" can each independently be an alkyl, aryl, alkenyl, an oligomer, or a polymer.

In some embodiments, the oxidizable material may be a metallic substrate. Preferably, the dihydropyridazine compound can inhibit or delay corrosion of the metallic substrate. In other embodiments, the oxidizable material may be an unsaturated compound, wherein the unsaturated compound is an unsaturated oil, an unsaturated lipid, an unsaturated fat, or an unsaturated monomer. For example, the oxidizable material may an unsaturated monomer, and the dihydropyridazine compound can inhibit or delay polymerization of the unsaturated monomer. Example of the unsaturated monomer include, but is not limited to, a styrenic monomer, an ethylene monomer, a propylene monomer, a vinylic monomer, a diene monomer, an acrylate monomer, or a monomer having one or more double bonds.

In one embodiment, the antioxidant can be added to the oxidizable material by generating the dihydropyridazine compound in-situ by reacting an analogous tetrazine precursor directly with the oxidizable material. In another embodiment, the antioxidant can be added to the oxidizable material by dissolving the dihydropyridazine compound in the oxidizable material. In yet embodiment, the antioxidant can be added to the oxidizable material by coating the oxidizable material with a film comprising said antioxidant.

In preferred embodiments, when undergoing an oxidation reaction, the dihydropyridazine has a change in its fluorescence as it is oxidized to its conjugated pyridazine. Without wishing to limit the invention to a particular theory or mechanism, this change in fluorescence can act as an indicator for the extent of oxidation. In one embodiment, the dihydropyridazine compound is configured to become UV fluorescent as it is oxidized to its conjugated pyridazine. In another embodiment, the dihydropyridazine compound is configured to become non-fluorescent as it is oxidized to its conjugated pyridazine.

In other preferred embodiments, the dihydropyridazine compound is capable of being regenerated by hydrogenation of its oxidized pyridazine form, thereby recycling the antioxidant and further delaying oxidation of the oxidizable material. Non-limiting procedures of regenerating the dihydropyridazine compound include undergoing a reduction reaction, a reaction with phosphines in water, a photochemical reduction, an electrochemical reduction, or a reaction with metal hydrides.

One of the unique and inventive technical features of the present invention is the use of dihydropyridazines as antioxidants or free radical reaction inhibitors. Without wishing to limit the present invention to a particular theory or mechanism, the dihydropyridazines can donate two equivalents of hydrogen atoms to terminate radical chain reactions or oxidation reactions. Further still, its oxidized pyridazine form may then be reduced to regenerate the dihydropyridazine, thus recycling the antioxidant and extending the time before polymers or other materials are oxidized. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

As known to one of ordinary skill in the art, a "radical" is a species having a single, unpaired electron. A radical species that is electrically neutral may be referred to as a "free radical". An "antioxidant" is a molecule that can inhibit the oxidation of other molecules. The term "inhibit" means to prevent, hinder, retard, delay, or slow down a chemical process.

As known to one of ordinary skill in the art, the term "unsaturated" refers a molecule having a double or triple bond, e.g. alkene or alkyne functional group. Unsaturated compounds include, but are not limited to, unsaturated oils, unsaturated lipids, unsaturated fats, and unsaturated monomers or polymer precursors. In some embodiments, unsaturated monomers can polymerize via chain radical polymerization of the alkenes. This is true for polymers such as polyethylene, polypropylene, polystyrene, and other vinylic polymers.

As known to one of ordinary skill in the art, the term "oxidizable material" refers to a material, compound or metal that is capable of undergoing a chemical oxidation reaction with oxygen or is capable of forming additional bonds to hydrogen. Non-limiting examples of oxidizable materials include food products, unsaturated compounds, pharmaceutical products, cosmetics, and ferrous metals.

As used herein, "dihydropyridazine" is a heterocyclic organic compound characterized in having two adjacent nitrogen atoms in its ring. It is structurally similar to benzene, with two methine groups (=CH—) replaced by nitrogen atoms. It has a basic chemical formula of $C_4H_6N_2$ and the carbon atoms may be optionally substituted with functional groups other than H. Thus, a compound containing a dihydropyridazine group is referred to herein as a dihydropyridazine compound. Dihydropyridazine compounds are also oxidizable and may be preferentially oxidized with respect to other oxidizable materials either because of a more kinetically or thermodynamically favored oxidation reaction or because of a superior number or position of the molecules available for oxidation.

In this present invention, dihydropyridazines are shown to act as antioxidants to retard oxidation of polymers or other materials by oxygen and other chemical oxidants, free radicals generation by thermal processes, degradation of peroxides, ultraviolet light or ionizing radiation or free radical initiators, and polymerization of vinyl monomers. In some embodiments, the antioxidant characteristics are obtained through the oxidative abstraction of two equivalents of hydrogen from the dihydropyridazine ring. Each hydrogen can react with a radical species to terminate a free radical chain mechanism, as shown in Scheme 1.

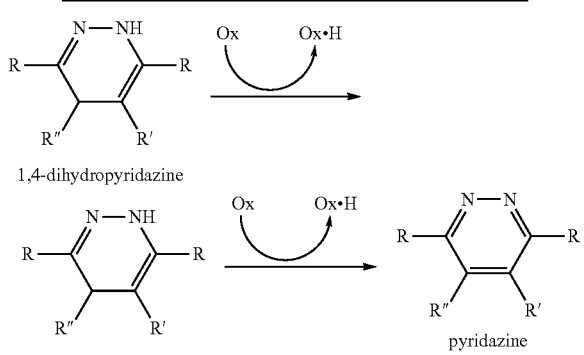

Scheme 1. Anti-oxidant mechanism of 1,4-dihydropyridazines to pyridazine.

Examples of R include, but are not limited to H, Cl, Br, F, OAlkyl, OAryl, SAlkyl, $NH_2$, NHAlkyl, NHAryl, NAlkyl$_2$, NHNH$_2$, N=CRR', vinyl, alkenyl, CO$_2$Alkyl, CO$_2$Aryl, CONH$_2$, CONHAlkyl, CONHAryl, CONAlkyl$_2$, CONAryl$_2$, CN, alkyl, aryl, pyridyl, oligomers, or polymers based on the same. Examples of R' include, but are not limited to alkyl, aryl, oligomers, or polymers based on the same. Examples of R" include, but are not limited to alkyl, aryl, oligomers, or polymers based on the same.

For example, 1,4-dihydropyridazines with any number of substituents at the 3,6-positions (Scheme 1, R) or at the 4,5-positions (Scheme 1, R' and R") can be used as antioxidants. These dihydropyridazines can be prepared from Carboni-Lindsey reaction of tetrazine precursors, from condensation of 1,4-diones or cyclic anhydrides with hydrazine, or by reduction of pyridazines. The ability to hydrogenate pyridazines to dihydropyridazines may provide for recycling and even longer effective lifetimes for materials being protected by the antioxidants. Antioxidants that can prolong a time period of a polymer to survive oxidative degradation would be highly desirable, particularly in applications where the antioxidants could also reduce potential health and environmental concerns. In an exemplary embodiment, about 1 mol % dihydropyridazine can delay the onset of free radical polymerization by ten times longer than an equivalent amount of dibutylhroxytoluene (BHT), the antioxidant often used in food, reactive monomers, and plastics. The antioxidant can be added as a small molecule of 1,4-dihydropyridazine to be dissolved into the media that is to be protected, or it can be generated in-situ by reacting the analogous tetrazine precursor with C=C bonds present in the material or in another additive.

For example, as shown in Scheme 2, an unsaturated fatty acid could be protected by adding several mol % of dimethyl-1,2,4,5-tetrazine dicarboxylate, which would react with the C=C bonds to form a 1,4-dihydropyridazine that is attached to the 1 mol % of the fatty acids.

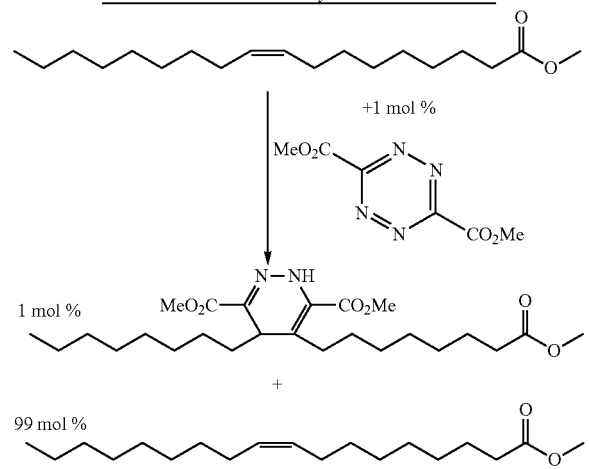

Scheme 2. Formation of 1,4-dihydropyridazine via a Carboni Lindsey reaction.

Furthermore, there is an observable change in fluorescent properties between dihydropyridazines and aromatic pyridazines that can be used to monitor or indicate the extent of oxidation. Without wishing to limit the invention to a particular theory or mechanism, the change in fluorescent properties may be substituent dependant. For instance, a 3,6-dichloropyridazine species fluoresces as it becomes oxidized to the more conjugated pyridazine, whereas other pyridazines are fluorescent as the dihydro species and become non-fluorescent once oxidized. As another example, an aryl, methyl, or methyl ester functionalized dihydropyridazines may fluoresce under UV light.

According to some embodiments, the present invention features antioxidant and free-radical inhibitor composition comprising a dihydropyridazine compound. In one embodiment, the dihydropyridazine compound is prepared by reacting tetrazine precursors with a polymer backbone having unreacted alkene functional groups. Without wishing to limit the invention to a particular theory or mechanism, the tetrazine precursors react with the alkene functional groups in the polymer backbone via a Carboni-Lindsey reaction, thereby covalently attaching a dihydropyridazine group to the polymer backbone. In some embodiments, a molar ratio of the tetrazine precursors to unreacted alkene functional groups can range from 1:4 to 1:1.

In one embodiment, the dihydropyridazine compound may be a 1,4-dihydropyridazine according to the formula:

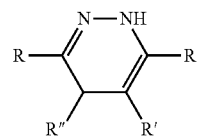

In some embodiments, R can be an H, Cl, Br, F, alkyl, aryl, pyridyl, O-alkyl, S-alkyl, S-aryl, $NH_2$, NH-Alkyl, NH-Aryl, N-(Alkyl)$_2$, N-(Aryl)$_2$, $NHNH_2$, N=CRR', vinyl, alkenyl, $CO_2$-Alkyl, $CO_2$-Aryl, $CONH_2$, CONH-Alkyl, CONH-Aryl, CON-(Alkyl)$_2$, CON-(Aryl)$_2$, or CN, and In some embodiments, R' and R" can each independently be an alkyl, aryl, alkenyl, an oligomer, or a polymer.

In some preferred embodiments, the composition may be used in a packaging material to inhibit oxidation of an oxidizable material that is packaged with the packaging material. The packaging material may be in the form of a sheet, box, bag, film or coating. Without wishing to limit the invention to a particular theory or mechanism, when the dihydropyridazine compound and oxidizable material are exposed to an oxidizing species, the dihydropyridazine compound can prevent or delay the oxidizing species from oxidizing the oxidizable material by being oxidized itself, instead of oxidizable material, thus consuming the oxidizing species.

Typically antioxidants are not added in amounts greater than 1-4 wt % because the antioxidants are not soluble at higher concentrations or the higher concentrations have adverse effects on flavor, mechanical properties, health, environment, or appearance. Without wishing to limit the invention to a particular theory or mechanism, by attaching the antioxidant to the polymer or the small molecule being protected, the solubility limitation is dramatically reduced or even eliminated. Further still, in the case of protecting polymers, attaching the antioxidant to the polymer can reduce the health and environmental concerns by anchoring the antioxidant so it can neither be extracted or leached from the polymer, nor lost due to vaporization. Without wishing to limit the invention to a particular theory or mechanism, the 1,4-dihydropyridazines may be used at 100 mol % or more, leading to extended lifetimes without oxidation and degradation.

As an example, modification of polybutadiene with 4 mol % dimethyl 1,2,4,5-tetrazine-3,6-dicarboxylate can covalently install four 1,4-dihydropyridazine groups for every 100 butadiene repeat units, an equivalent of 15 wt % antioxidant, as shown in Scheme 3. At 4 mol % modification, the polymer would still be an elastomer, but would have almost four times the antioxidant protection of BHT.

Scheme 3. Reaction of 1,4-dihydropyridazine and polybutadiene.

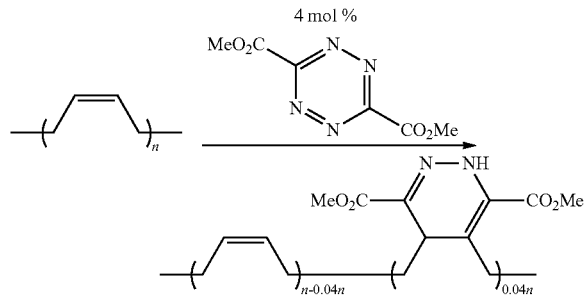

The dihydropyridazine compounds have been shown to act as antioxidants and free radical inhibitors, as described above. Thus, in one aspect, it is an objective of the invention to provide for methods of using dihydropyridazines as such.

According to one embodiment, the present invention features a method for inhibiting oxidation of an unsaturated compound. The method may comprise adding any one of the dihydropyridazine compounds disclosed herein to the unsaturated compound. Preferably, an amount of said dihydropyridazine compound is sufficient to inhibit oxidation of said unsaturated compound. In some embodiments, the unsaturated compound may be an unsaturated oil, an unsaturated lipid, an unsaturated fat, or an unsaturated monomer.

According to another embodiment, the present invention features a method of inhibiting free radical polymerization of unsaturated monomers. The method may comprise any one of the dihydropyridazine compounds disclosed herein to the unsaturated monomers. Preferably, an amount of said dihydropyridazine compound is sufficient to inhibit free radical polymerization of said unsaturated monomers. In one embodiment, the unsaturated monomers may comprise an alkene moiety. In another embodiment, the unsaturated monomers may be styrene monomers, ethylene monomers, propylene monomers, vinylic monomers, and the like.

In some embodiments, the dihydropyridazine compound may be prepared by reacting tetrazine precursors with a polymer backbone having unreacted alkene functional groups, wherein the tetrazine precursors react with the alkene functional groups in the polymer backbone via a Carboni-Lindsey reaction, thereby covalently attaching a dihydropyridazine group to the polymer backbone. In one embodiment, the polymer backbone is identical to the unsaturated compound or unsaturated monomers. In another embodiment, the polymer backbone is different from the unsaturated compound or unsaturated monomers.

According to another embodiment, the present invention features a method for inhibiting corrosion of a metallic substrate. The method may comprise coating the metallic substrate with a film comprising any one of the dihydropyridazine compounds disclosed herein. For example, the metallic substrate is coated with a liquid that dries and forms a thin protective film on the metallic substrate. In a preferred embodiment, an amount of said dihydropyridazine compound is sufficient to inhibit the corrosion, such as rusting or pitting, of the metallic substrate. In some embodiments, the metallic substrate may be constructed from a ferrous material, carbon steel, stainless steel, brass, copper, alloys thereof, and the like. Examples of metallic substrates include, but are not limited to, metal sheeting, metal pipes, metal rods, metal studs, metal fasteners, metal furniture, metal containers, and metal parts for vehicles or machinery.

In yet another embodiment, the present invention features a method of producing a packaging material. In some embodiments, the packaging material is manufactured to be in the form of a sheet. In preferred embodiments, the method may comprise applying an antioxidant to the entire surface of the packaging material sheet. In more preferred embodiments, the antioxidant may comprise any one of the dihydropyridazine compounds disclosed herein in an amount sufficient to inhibit oxidation of a substance that is packaged in the packaging material sheet. For example, the packaging material sheet may be used as a packaging container for a food substance, such as for example, breads, cereals, grains, candy, noodles, pasta, crackers, and chips. In other embodiments, the packaging material sheet may be used as a packaging container for oils, fats, milks, and other substances that are prone to becoming rancid.

In some embodiments, the present invention features a method for stabilizing a reactive chemical composition. The method may comprise adding any one of the compounds disclosed herein to the reactive chemical composition. The dihydropyridazine compound may be added in an amount that is sufficient to inhibit oxidation and free radical chain reactions from occurring in the reactive chemical composition.

According to other embodiments, the present invention features a method of preparing a composition having antioxidant properties. The method may comprise adding any one of the dihydropyridazine compounds disclosed herein to the composition. Preferably, an amount of the dihydropyridazine compound is sufficient to inhibit oxidation and free radical chain reactions.

In some embodiments, for any of the methods described herein, the dihydropyridazine compound may be prepared by reacting tetrazine precursors with a polymer backbone having unreacted alkene functional groups, wherein the tetrazine precursors react with the alkene functional groups in the polymer backbone via a Carboni-Lindsey reaction, thereby covalently attaching a dihydropyridazine group to the polymer backbone. In other embodiments, when undergoing an oxidation reaction, the dihydropyridazine compound is configured to become UV fluorescent as it is oxidized to a conjugated pyridazine. Alternatively, when undergoing an oxidation reaction, the dihydropyridazine compound may become non-fluorescent as it is oxidized to a conjugated pyridazine. In either case, the change in fluorescent properties between dihydropyridazines and pyridazines can function as an indicator for extent of oxidation. In still other embodiments, the dihydropyridazine compound is configured to be regenerated by undergoing a reduction reaction.

In further embodiments, the variety of different substituents and level of hydrogenation can provide diversity in solubility to allow the dihydropyridazine antioxidants to be soluble in practically any commercial polymer, including polymers used for protective coatings for preventing metal corrosion.

In exemplary embodiments, the dihydropyridazines may be added to vinyl monomers as free radical polymerization inhibitors to prevent the monomers from prematurely polymerizing. In the examples that follow, the ability of dihydropyridazine in delaying the onset of free radical initiated polymerization of divinyl benzene initiated by 1 mol % azoisobutyronitrile (AIBN) is demonstrated.

EXAMPLES

The following are non-limiting examples of the present invention, in particular, the use of dihydropyridazines as an antioxidant. The examples are for illustrative purposes only and are not intended to limit the invention in any way. Equivalents or substitutes are within the scope of the invention.

Oxidation of non-fluorescent 1,4-dihydropyridazines removes two hydrogens and affords aromatic pyridazines that fluoresce white under ultraviolet light. A variety of oxidants can be used, but air oxidation is use herein. Films of poly(1,4-dihydropyridazine) become UV fluorescent after being exposed to ambient light in air for days. Confirmation of the antioxidant properties of dihydropyridazines was obtained by observing their influence at 1 mol % on the polymerization and gelation of divinylbenzene and styrene with 1 mol % AIBN at 70° C. Without antioxidant, the monomers polymerized to form glassy gels in 11 minutes. With 1 mol % BHT, gelation was delayed until 13 minutes. With 1 mol % of 3,6-dichloro-1,2,4,5-tetrazine (DCT) added to the styrene to form the dihydropyridazine, then mixed with divinylbenzene and polymerized, gels formed after 20 min. With 1 mol % of 3,6-Dimethyl-1,2,4,5-tetrazine (DMDT), gels formed only after 160 minutes.

Scheme 4. Addition of tetrazine to free radical polymerization of divinylbenzene.

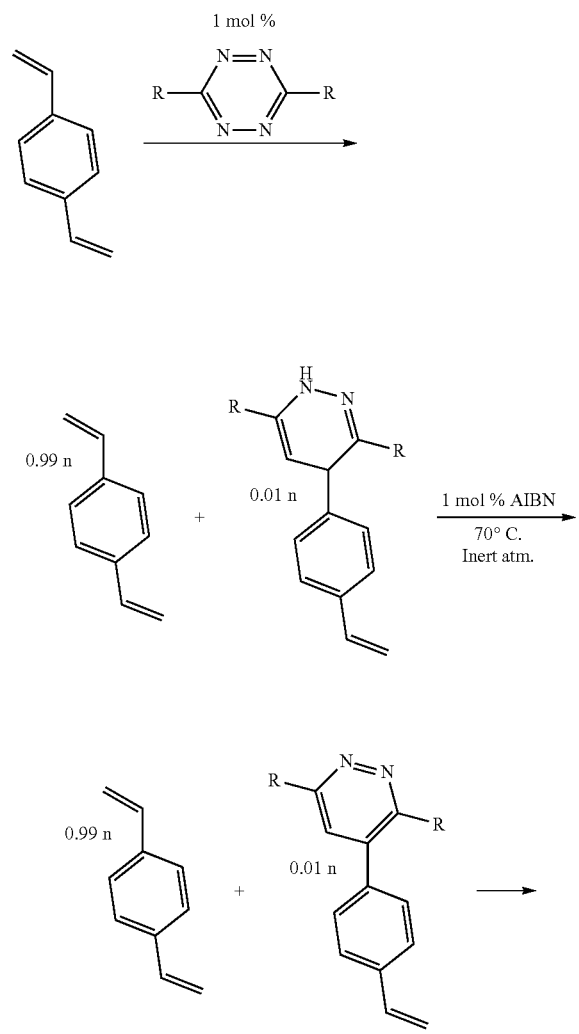

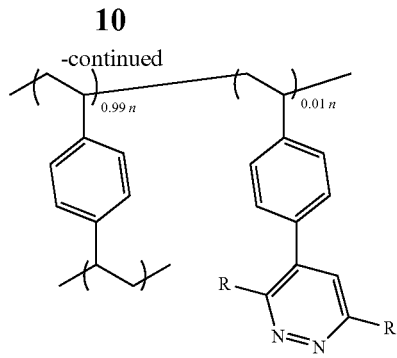

Normally, the free radical polymerization of divinylbenzene and styrene rapidly leads to gels, providing a visual indication of free radical polymerization. In the aforementioned examples, the relative effectiveness of free radical inhibitors are determined by how much a standard quantity delays the onset of gelation. In the presence of 1 mol % AIBN, divinylbenzene will polymerize with crosslinking to form a gel in 11 minutes. Addition of 1 mol % BHT delays gelation to 13 minutes. With 1 mol % of DMDT, gelation of divinylbenzene was delayed to 160 minutes or 14× longer than without the inhibitor, and 12× longer than with an equivalent amount of BHT.

While polymer degradation can be delayed by the addition of existing antioxidants, such as BHT, the present invention can provide an antioxidant that can at least double the time that the polymer can survive oxidative degradation. Furthermore, the antioxidants of the present invention can also reduce potential health and environmental concerns.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for inhibiting or delaying oxidation of an oxidizable material, comprising adding an antioxidant to the oxidizable material, wherein the antioxidant comprises a dihydropyridazine compound, wherein the dihydropyridazine compound is a 1,4-dihydropyridazine according to the formula:

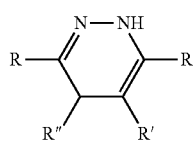

wherein R is an H, Cl, Br, F, alkyl, aryl, O-alkyl, S-alkyl, S-aryl, $NH_2$, NH-Alkyl, NH-Aryl, N-(Alkyl)$_2$, N-(Aryl)$_2$, $NHNH_2$, N=CRR', vinyl, alkenyl, $CO_2$-Alkyl, $CO_2$-Aryl, $CONH_2$, CONH-Alkyl, CONH-Aryl, CON-(Alkyl)$_2$, CON-(Aryl)$_2$, or CN, and wherein R' and R" are each independently an alkyl, aryl, alkenyl, an oligomer, or a polymer, wherein when the dihydropyridazine compound and oxidizable material are exposed to an oxidizing species, the dihydropyridazine compound is oxidized to consume the oxidizing species, thereby preventing or hindering the oxidizing species from oxidizing the oxidizable material wherein an amount of said dihydropyridazine compound is sufficient to inhibit or delay oxidation of said oxidizable material, wherein the oxidizable material is an unsaturated compound, wherein the unsaturated compound is an unsaturated oil, an unsaturated lipid, an unsaturated fat, or an unsaturated monomer.

2. The method of claim 1, wherein the unsaturated compound is an unsaturated monomer, wherein the dihydropyridazine compound inhibits or delays polymerization of the unsaturated monomer.

3. The method of claim 2, wherein the unsaturated monomer is a styrenic monomer, an ethylene monomer, a propylene monomer, a vinylic monomer, a diene monomer, an acrylate monomer, or a monomer having one or more double bonds.

4. A method for inhibiting or delaying oxidation of an oxidizable material, comprising adding an antioxidant to the oxidizable material, wherein the antioxidant comprises a dihydropyridazine compound, wherein adding the antioxidant to the oxidizable material comprises dissolving the dihydropyridazine compound in the oxidizable material, wherein the dihydropyridazine compound is a 1,4-dihydropyridazine according to the formula:

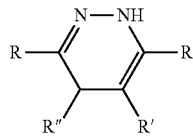

wherein R is an H, Cl, Br, F, alkyl, aryl, O-alkyl, S-alkyl, S-aryl, $NH_2$, NH-Alkyl, NH-Aryl, N-(Alkyl)$_2$, N-(Aryl)$_2$, $NHNH_2$, N=CRR', vinyl, alkenyl, $CO_2$-Alkyl, $CO_2$-Aryl, $CONH_2$, CONH-Alkyl, CONH-Aryl, CON-(Alkyl)$_2$, CON-(Aryl)$_2$, or CN, and wherein R' and R" are each independently an alkyl, aryl, alkenyl, an oligomer, or a polymer, wherein when the dihydropyridazine compound and oxidizable material are exposed to an oxidizing species, the dihydropyridazine compound is oxidized to consume the oxidizing species, thereby preventing or hindering the oxidizing species from oxidizing the oxidizable material, wherein an amount of said dihydropyridazine compound is sufficient to inhibit or delay oxidation of said oxidizable material.

5. A method for inhibiting or delaying oxidation of an oxidizable material, comprising adding an antioxidant to the oxidizable material, wherein the antioxidant comprises a dihydropyridazine compound, wherein adding the antioxidant to the oxidizable material comprises coating the oxidizable material with a film comprising said antioxidant, wherein the dihydropyridazine compound is a 1,4-dihydropyridazine according to the formula:

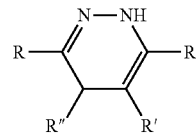

wherein R is an H, Cl, Br, F, alkyl, aryl, O-alkyl, S-alkyl, S-aryl, $NH_2$, NH-Alkyl, NH-Aryl, N-(Alkyl)$_2$, N-(Aryl)$_2$, $NHNH_2$, N=CRR', vinyl, alkenyl, $CO_2$-Alkyl, $CO_2$-Aryl, $CONH_2$, CONH-Alkyl, CONH-Aryl, CON-(Alkyl)$_2$, CON-(Aryl)$_2$, or CN, and wherein R' and R" are each independently an alkyl, aryl, alkenyl, an oligomer, or a polymer, wherein when the dihydropyridazine compound and oxidizable material are exposed to an oxidizing species, the dihydropyridazine compound is oxidized to consume the oxidizing species, thereby preventing or hindering the oxidizing species from oxidizing the oxidizable material, wherein an amount of said dihydropyridazine compound is sufficient to inhibit or delay oxidation of said oxidizable material.

6. The method of claim 5, wherein the oxidizable material is a metallic substrate, wherein adding the antioxidant to the oxidizable material comprises coating the metallic substrate with the film comprising the dihydropyridazine compound, wherein the dihydropyridazine compound inhibits or delays corrosion of the metallic substrate.

* * * * *